United States Patent [19]

Steiner et al.

[11] Patent Number: 4,818,231
[45] Date of Patent: Apr. 4, 1989

[54] PROCESSING DEVICE FOR LOCAL IRRADIATION WITH VISIBLE OR INVISIBLE LIGHT

[75] Inventors: Hans Steiner, Germering; Alois Mitterndorfer, Schönberg, both of Fed. Rep. of Germany

[73] Assignee: Wilhelm Sedlbauer GmbH, Fed. Rep. of Germany

[21] Appl. No.: 25,142

[22] PCT Filed: May 9, 1986

[86] PCT No.: PCT/DE86/00191
§ 371 Date: Jan. 23, 1987
§ 102(e) Date: Jan. 23, 1987

[87] PCT Pub. No.: WO86/06614
PCT Pub. Date: Nov. 20, 1986

[30] Foreign Application Priority Data

May 9, 1985 [DE] Fed. Rep. of Germany ....... 3516774

[51] Int. Cl.[4] .............................................. A61C 5/00
[52] U.S. Cl. ...................................... 433/215; 433/32; 433/229
[58] Field of Search .......................... 433/32, 215, 229

[56] References Cited

U.S. PATENT DOCUMENTS

| 3,109,238 | 11/1963 | Marks . | |
|---|---|---|---|
| 3,509,629 | 5/1970 | Kidokoro et al. | 433/114 |
| 4,445,858 | 5/1984 | Johnson | 433/229 |

FOREIGN PATENT DOCUMENTS

| 3312 | 1/1979 | European Pat. Off. | 433/229 |
|---|---|---|---|
| 0027959 | 5/1981 | European Pat. Off. . | |
| 0166364 | 1/1986 | European Pat. Off. . | |
| 1602892 | 3/1971 | France . | |
| 2552592 | 3/1985 | France . | |

OTHER PUBLICATIONS

Radio Fernsehen Elektronik, vol. 27, Issue 4, 1978, pp. 263-264.

Primary Examiner—Robert Peshock
Attorney, Agent, or Firm—Steele, Gould & Fried

[57] ABSTRACT

A hand held device for providing local irradiation with visible or invisible light to defined processing points of tooth fillings for hardening tooth fillings during dental treatment includes a housing containing a light source for emitting visible or invisible light, a light conductor optically coupled to the light source which transmits visible or invisible light to the processing points, a fan for cooling the light source and a rechargeable battery and means for counting the times the light source is activated.

16 Claims, 1 Drawing Sheet

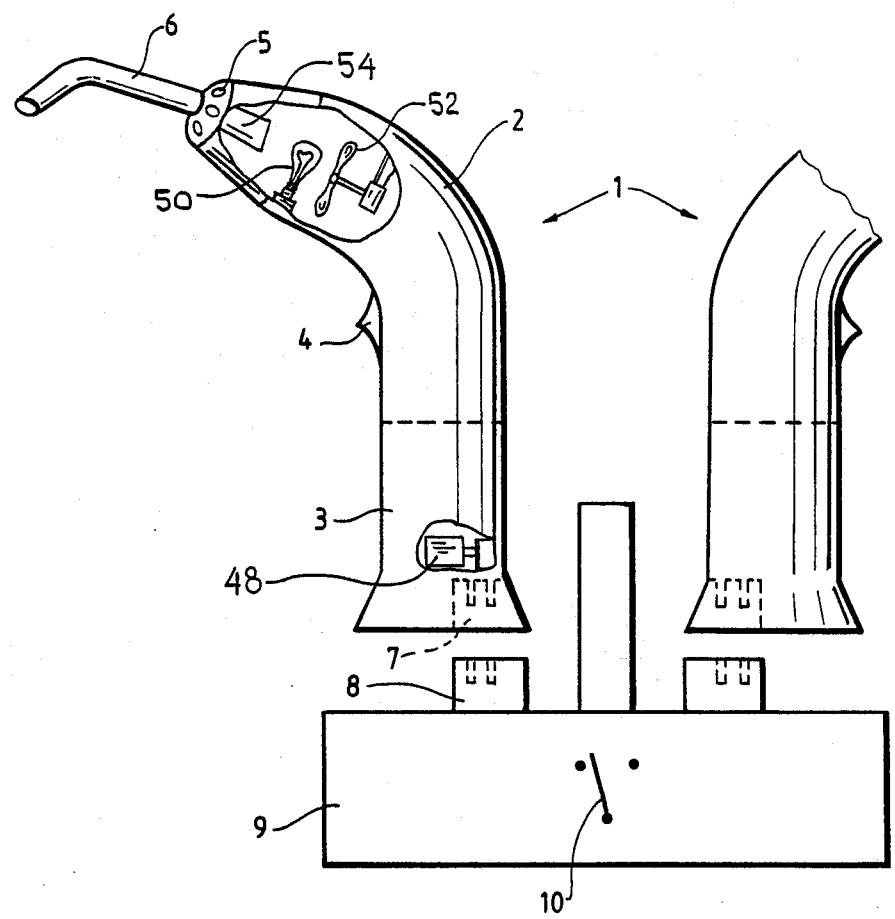

PROCESSING DEVICE FOR LOCAL IRRADIATION WITH VISIBLE OR INVISIBLE LIGHT

The present invention refers to a processing device for local irradiation of defined processing points with visible or invisible light. Devices of this type are primarily needed as treatment devices in dental medicine for hardening of tooth fillings, where masses of synthetic material are hardened by means of visible light but also by means of infrared light.

While initially the light rays from a light source were guided onto the treatment point via a relatively long light conductor, one currently accommodates the light source in a hand-held device according to a more recent development, said hand-held device having a rigid light carrier at its head. Thereby, the light beams generated by the light source are transferred in the interior of the hand-held device via the light conductor and by means of corresponding optical coupling elements to the processing or treatment point. Thereby, a fan is normally also accommodated in the processing device in order to sufficiently cool the light source, which has a relatively high power draw.

A disadvantage of the treatment with a device of this nature is the required power supply cable, which, particularly in the case of a device for dental medicine, must be inserted in the most varying spatial positions in order to harden the fillings even at inaccessible points in the mouth of a patient.

The purpose of the invention is to further develop a treatment device of this type so that the handling thereof is facilitated without any loss of efficiency of the irradiation proper.

This problem is solved by means of a processing device with the characteristics of patent claim 1.

Consequently, in the treatment device according to the invention, batteries are accommodated in the hand-held device proper, particularly rechargeable batteries, so-called accumulators. Since a precisely defined quantity of light with precisely defined intensity is always required for the hardening, a particularly advantageous further development of the invention concept also provides a voltage control device in the hand-held device, which control device immediately prevents the handling of the device if a pre-set terminal voltage on the batteries or accumulators is not reached, since the possibility exists that the desired and necessary hardening of the filling would not be guaranteed if the device were used under such conditions.

According to another further development of the invention concept, it is also possible to include a counter, if necessary of a mechanical nature, in addition to the voltage control device or instead of this, which counter registers the number of uses of the device, whereby, since each individual use covers a precisely defined time, it is very easy to establish when the counter must block further use of the device without need for high cost electronic monitoring devices. A counter of this type, which would show the dentist that a full recharge of the device is needed prior to use, possibly by eliminating the readiness of the device for use if this is required, would then only have to be reset after the charging process, and the device can then be used again in the same manner for the anticipated number of treatments.

Further details of a treatment device according to the invention will be explained in the following with reference to the enclosed drawing.

BRIEF DESCRIPTION OF THE DRAWINGS

In the drawing, FIG. 1 indicates a treatment or processing device in general. Thereby, it is assumed that an individual dentist owns at least two processing devices of this type, which can be placed on a charger 9 which is common for both devices.

Each individual processing device consists of a housing 2, with an attached housing part 3, in which rechargeable batteries 48 are accommodated.

In the upper portion of the housing 2, a light source 50 and a fan 52 are accommodated in a manner known per se. At the head 5, a light conductor 6 is attached, by means of which the light generated by the light source in the interior of the housing 2 is transmitted to the treatment point via optical coupling elements 54. The light conductor proper may be rigid (of glass) or also capable of being bent plastically (of a synthetic material).

At least the activation of the light source is achieved by means of the switch 4, which is represented as a slide switch. Thereby, it is also possible that a timer switch provided in the interior of the device deactivates it in a forced sequence or via the switch 4, whereby the end of the time needed for correct hardening is indicated to the dentist.

A connection unit 7, which is only indicated by means of a dashed line, is built into the foot of the housing, where the batteries or accumulators are accommodated. This connection unit 7 is developed so that it can cofunction with a contact unit 8 on the charger 9, so that an electrical connection is immediately established when the hand-held device 1 is placed on the charger, so that the charging process can take place.

A switch 10 schematically indicates that only one of the two processing devices 1 can be charged at any one time, e.g. that device which is shown either to the left or to the right.

The expert with experience in the field will then see that the charger naturally can be equipped with indicators of the most varying kinds for the charge condition of the individual devices, e.g. for the charging time, the charge capacity, or the terminal voltage, whereby an indication by means of LCD is also possible. Thereby, practice has shown that it is particularly advantageous to use so many batteries that the terminal voltage is 14.2 V with a current delivery of approx. 7.5 A.

If, as already indicated, the device is thereby placed on the charger only after a predetermined number of uses, namely generally with an activation of the light source for 20 seconds per use, the individual batteries will be particularly well maintained, since they will always be fully charged and fully discharged.

In order to avoid an overcharge of the individual devices, the device can be automated in a manner known per se, namely so that after the charging with the charge current proper, there is an automatic switch-over to charge maintenance. This is particularly recommended when the charge takes place during longer pauses in the treatment, e.g. over night.

For the execution of the invention, no conditions and consequently also no limits exist with respect to the the shape of the individual devices.

We claim:

1. A hand held processing device for local irradiation, with visible or invisible light, of defined processing points of tooth fillings for hardening the tooth fillings during a dental treatment, said hand-held device comprising:
   a housing, within which is disposed:
   a light source means for emitting said visible or invisible light;
   a light conductor optically coupled to said light source means via an optical coupling element, said light conductor transmitting said light to said processing points;
   a fan means for cooling said light source;
   at least one rechargeable battery means for supplying power to said light source means and said fan means and;
   means for counting the number of times said light source is activated and for preventing further activation thereof when the count exceeds a predetermined number until said batteries have been recharged.

2. Processing device according to claim 1, characterized in that the batteries are accommodated in a foot portion of the housing and said light conductor is made of a material having a characteristic selected from the group of rigid and plastic.

3. Processing device according to claim 1 including a plug-in device means, secured against contact, provided in an area of the foot portion of the housing, on the bottom side thereof, for inserting the processing device into a charger.

4. Processing device according to claim 1 including means, coupled to the battery, for preventing the activation of the light source if a terminal voltage of the battery is lower than a predetermined minimum value.

5. Processing device according to claim 1, wherein said means for counting includes a counter means, coupled to an activator means for the device, for preventing further activation after said predetermined number of activations until a charging process has been completed.

6. Processing device according to claim 1, wherein a charger, external to said housing, is to be provided and includes means for accommodating several, preferably two processing devices.

7. Processing device according to claim 6, wherein the charger includes a switch that allows only one of the devices to be charged at any one time.

8. Processing device according to claim 6, wherein a charge maintenance device is provided in the charger in order to maintain the charge of those batteries in said several processing devices which are not at that particular time connected to a charge voltage.

9. A hand held processing device for local irradiation, with visible or invisible light, of defined processing points of tooth fillings for hardening the tooth filings during a dental treatment, said hand-held device comprising:
   a housing, within which is disposed:
   a light source means for emitting said visible or invisible light;
   a light conductor optically coupled to said light source means via an optical coupling element, said light conductor transmitting said light to said processing points;
   a fan means for cooling said light source;
   at least one rechargeable battery means for supplying power to said light source means and said fan means; and
   means for monitoring a terminal voltage of said battery and for preventing the activation of the light source if said terminal voltage of the battery is lower than a predetermined minimum value.

10. Processing device according to claim 9, characterized in that the batteries are accommodated in a foot portion of the housing and said light conductor is made of a material having a characteristic selected from the group of rigid and plastic.

11. Processing device according to claim 9 including a plug-in device means, secured against contact, provided in an area of the foot portion of the housing, on the bottom side thereof, for inserting the processing device into a charger.

12. Processing device according to claim 9, wherein said means for monitoring is a stabilizing charge monitor switching means, coupled to the battery, for preventing the activation of the light source if said terminal voltage of the battery is lower than said predetermined minimum value.

13. Processing device according to claim 12, including a counter means, coupled to an activator means for the device, for preventing further activation after a predetermined number of activations until a charging process has been completed.

14. Processing device according to claim 9, wherein a charger, external to said housing, is provided and includes means for accommodating several, preferably two processing devices.

15. Processing device according to claim 14, wherein the charger includes a switch that allows only one of the devices to be charged at any one time.

16. Processing device according to claim 14, wherein a charge maintenance device is provided in the charger in order to maintain the charge of those batteries in said several processing devices which are not at that particular time connected to a charge voltage.

* * * * *